United States Patent
Jackson et al.

(10) Patent No.: US 7,014,631 B2
(45) Date of Patent: Mar. 21, 2006

(54) ELASTIC CLOSURE TAB

(75) Inventors: Byron M. Jackson, Forest Lake, MN (US); Leigh E. Wood, Woodbury, MN (US); Roderick L. Storey, Vadnais Heights, MN (US); James V. Metz, Maplewood, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 161 days.

(21) Appl. No.: 10/121,458

(22) Filed: Apr. 12, 2002

(65) Prior Publication Data

US 2003/0194936 A1 Oct. 16, 2003

(51) Int. Cl.
*A61F 13/58* (2006.01)

(52) U.S. Cl. .................. 604/389; 428/40.1; 428/195.1; 428/343; 428/354; 442/149; 442/151; 442/328; 442/394

(58) Field of Classification Search ................. 604/389; 428/343, 354, 40.1, 195.1; 442/149, 151, 442/328, 394
See application file for complete search history.

(56) References Cited

U.S. PATENT DOCUMENTS

| | | | |
|---|---|---|---|
| 3,265,765 A | 8/1966 | Holden et al. | |
| 3,562,356 A | 2/1971 | Nyberg et al. | |
| 3,700,633 A | 10/1972 | Wald et al. | |
| 3,800,796 A | 4/1974 | Jacob | |
| 4,116,917 A | 9/1978 | Eckert | |
| 4,156,673 A | 5/1979 | Eckert | |
| 4,522,853 A | 6/1985 | Szonn et al. | |
| 4,643,729 A | 2/1987 | Laplanche | |
| 4,778,701 A | 10/1988 | Pape et al. | |
| 4,787,897 A * | 11/1988 | Torimae et al. | ............. 604/389 |
| 4,795,456 A | 1/1989 | Borgers et al. | |
| 4,834,820 A | 5/1989 | Kondo et al. | |
| 5,057,097 A | 10/1991 | Gesp | |
| 5,344,691 A | 9/1994 | Hanschen et al. | |
| 5,468,428 A * | 11/1995 | Hanschen et al. | .......... 264/483 |
| 5,773,374 A | 6/1998 | Wood et al. | |
| 6,463,633 B1 | 10/2002 | Sangani et al. | |

FOREIGN PATENT DOCUMENTS

| | | |
|---|---|---|
| EP | 0 832 630 B1 | 4/1998 |
| EP | 0891760 | 1/1999 |
| EP | 1133967 | 9/2001 |
| JP | HEI 4-1117059 | 3/1992 |
| WO | WO 96/02218 | 2/1996 |
| WO | WO 01/68025 A1 | 9/2001 |

* cited by examiner

Primary Examiner—Daniel Zirker
(74) Attorney, Agent, or Firm—William J. Bond

(57) ABSTRACT

There is provided a nonwoven elastic laminate closure tab of the invention comprising adjacent first and second nonwoven closure elements each having a first face and a second face and a coextruded film elastic attached to each closure element first face. The first face of each closure element has a first area coated with a pressure sensitive adhesive and a second area adjacent the first area free of pressure-sensitive adhesive at terminal ends of the nonwoven closure elements. The coextruded film elastic has two first regions each having at least one inelastic zone and a second region between the two first regions having at least one elastic zone. The two opposing first regions are attached to the two pressure-sensitive adhesive areas of the two closure elements respectively such that the second adhesive free areas of the two adjacent closure elements are in face to face contact with at least a portion of the coextruded elastic film elastic second region. The layers are all of a thickness such that the thickness variation across the closure tab is less than 50%.

28 Claims, 3 Drawing Sheets

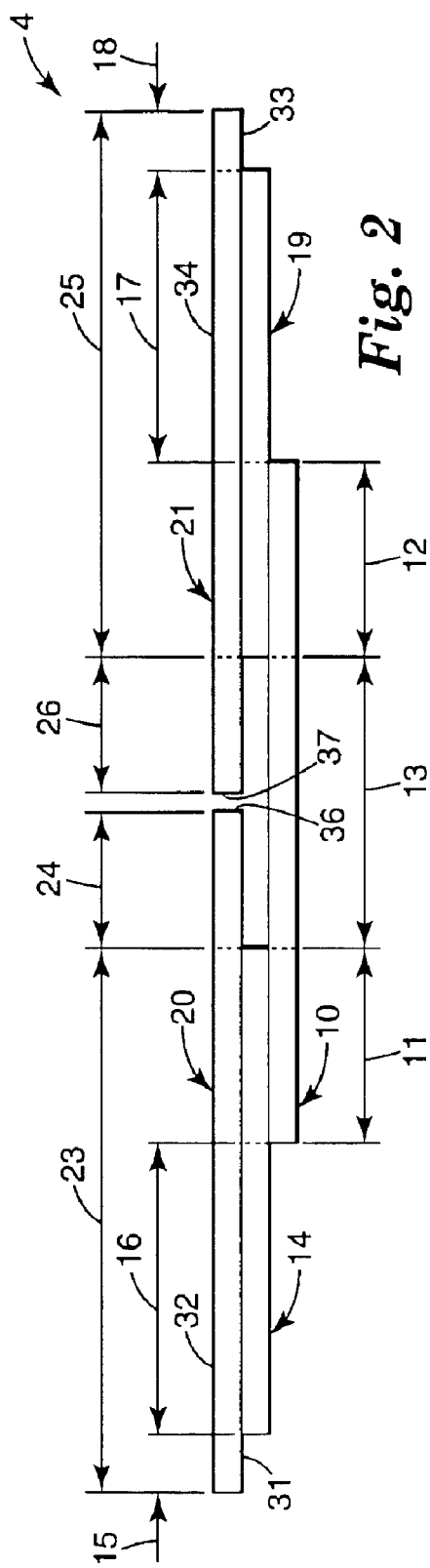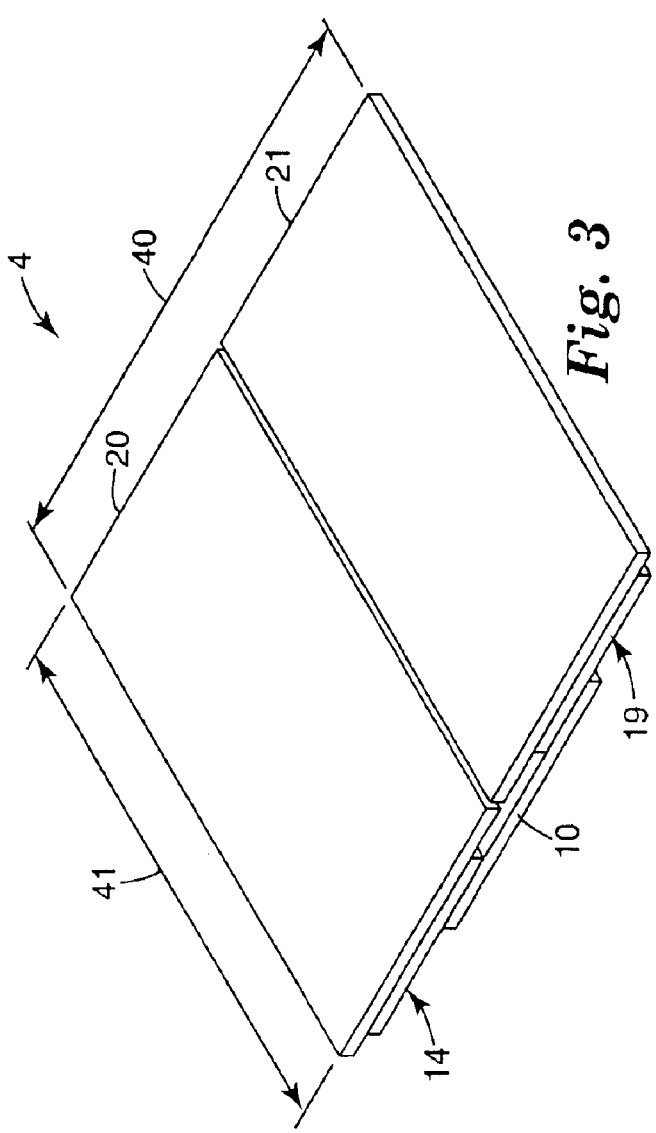

ELASTIC CLOSURE TAB

BACKGROUND OF THE INVENTION

The present invention relates to a novel elasticated fastener laminate for use in disposable absorbent articles and the like.

Disposable absorbent articles often use tab fasteners that are provided with elastic to allow for adjustment in the fit and a more secure and snug fit. For example, U.S. Pat. No. 3,800,796 (Jacob) teaches disposable diapers with elastic tabs wherein the tabs have an elastic segment between two inelastic segments. One of the inelastic segments is used to attach the tab to the diaper and the other inelastic segment has a PSA to allow the tab to close the diaper. The tab can be made such that the entire tab is formed of an elastic material and the two terminal segments are rendered inelastic, for example by laminating an inelastic material to the end segments. In Jacob, the elastic would be exposed to the adhesive if a tab precursor laminate were directly wound into a roll. This is problematic in that elastics generally can become permanently bonded to or contaminated by adhesives. This construction does not protect the elastic from direct contact with the adhesive. Further, the tabs vary in thickness which would inhibit the formation of a stable roll of the precursor tab fasteners laminate.

U.S. Pat. No. 4,522,853 (Szonn) also discloses an elastic tab adhesive closure for disposable diapers. The tabs disclosed in this patent have an intermediate (middle) elastic piece and adhesive coated end portions. The tab disclosed and claimed is complex and includes multiple additional elements. Szonn again does not protect its elastic from direct contact with adhesive layers. The constructions disclosed in Szonn are complicated and have multiple different layers that would result in considerable variation in the tab thickness making stable roll formation difficult.

U.S. Pat. No. 4,643,729 (Laplanche) also discloses a complex elastic fastener for disposable diapers that comprises three parts. These are, a first lateral side part (inelastic, for attaching to the diaper during manufacturing), a second lateral side part (inelastic, containing PSA for closing the diaper), and an elastic central part. The two lateral parts are parts of a single piece composed of a support band provided with a transverse precut line, which are separated at the time of use (along the pre-cut line). The two lateral parts are bonded to the central elastic part with adhesive bands and the lateral parts also have adhesive on the face opposite the elastic part for bonding to the diaper (one end for manufacturers bond the other end for closing the diaper in use). The elastic tabs taught in Laplanche again would not protect its elastic material from adhesive contact when wound in a roll.

U.S. Pat. No. 4,778,701 (Pape) discloses a roll of laminated strips from which separate elastic closure tabs can be cut. This is a pre-laminated elastic tab closure with a central elastic portion and inelastic end portions, one for attaching to the diaper during manufacturing and one for the consumer to use to close the diaper. The elastic in Pape is also not protected from exposure to the adhesive without an extra piece of protective material. The thickness of this material would also vary significantly over the width of the tab which is undesirable.

U.S. Pat. No. 4,795,456 (Borgers) discloses an extensible tab for disposable diapers that is stabilized (inextensible) until the user deploys the tab for diapering. This inextensibility of the elastic central segment is achieved by the tab construction including a non-extensible web (e.g. a release tape or liner) that bridges the inextensible end segments (as does the elastic segment) until the tab is opened for use. In Borgers, the elastic is again not protected from the adhesive. Also, the construction requires multiple adhesive layers and film layers such that it would be costly and difficult to manufacture.

U.S. Pat. No. 4,834,820 (Kondo) discloses an elastic diaper closure tab containing an elastic sheet and an inelastic retaining sheet which is directly bonded to the elastic sheet in the terminal end regions and the inelastic sheet has a cut-off groove in the center portion. When using the diaper the consumer manually rips apart the retaining sheet along the cut-off groove, whereupon the center of the elastic sheet is made flexible (elastic) as the retaining sheet no longer bridges the elastic sheet between the areas where the retaining sheet and the elastic sheet are bonded. The tab further has adhesive on the underside of the elastic sheet to anchor the tab to the side of the diaper (manufacturers bond) and to be used for closing the diaper. The structures (elastic tabs) taught in Kondo again require multiple layers of adhesive and fails to protect the elastic from direct contact with the adhesive layers if wound into a roll.

U.S. Pat. No. 5,057,097 (Gesp) discloses elastic diaper tape tabs wherein there is adhesive on the end segments and a central segment free of adhesive, and wherein the tape backing is a multilayer elastic film (e.g. a co-extruded elastic with inelastic skin layers). In Gesp, the elastic is protected from direct exposure to the adhesive layers but the terminal portions are not necessarily inelastic as the entire tab is generally elastic which could result in the tab failing during use. Also, the elastic is always exposed prior to use.

HEI 4[1992]-17059 (Sho 59[1984]-67022/Kokei No. Sho 60-215803, Hida) discloses a tab for disposable diapers having non-extensible end regions and an extensible sheet that connects the end regions and in which at least one part of the overlapping area of the end members and the extensible sheet are non-bonded. Again, the elastic in this construction is not protected from contact with the adhesive if wound into a roll form and a complicated multiple step construction process is required.

There is a need for a tab construction utilizing an elastic central region where the terminal ends are inelastic, which tab is easy to manufacture and provide in a stable roll form and where the elastic is simultaneous securely attached to the inelastic region and protected from direct contact with adhesive if wound into a roll while providing excellent aesthetic features.

SUMMARY OF THE INVENTION

The nonwoven elastic laminate closure tab of the invention comprises adjacent first and second nonwoven closure elements each having a first face and a second face and a coextruded film elastic attached to each closure element first face. The first face of each closure element has a first area coated with a pressure sensitive adhesive and a second area adjacent the first area free of pressure-sensitive adhesive at terminal ends of the nonwoven closure elements. The coextruded film elastic has two first regions each having at least one inelastic zone and a second region between the two first regions having at least one elastic zone. The two opposing first regions are attached to the two pressure-sensitive adhesive areas of the two closure elements respectively such that the second adhesive free areas of the two adjacent closure elements are in face to face contact with at least a portion of the coextruded elastic film elastic second region. The layers are all of a thickness such that the thickness variation across the closure tab is less than 50%.

DESCRIPTION OF THE DRAWINGS

FIG. 2 is a side view of the invention tab closure.

FIG. 3 is a side perspective of the invention tab closure.

DETAILED DESCRIPTION OF THE PREFERRED EMBODIMENT

Figure 1:
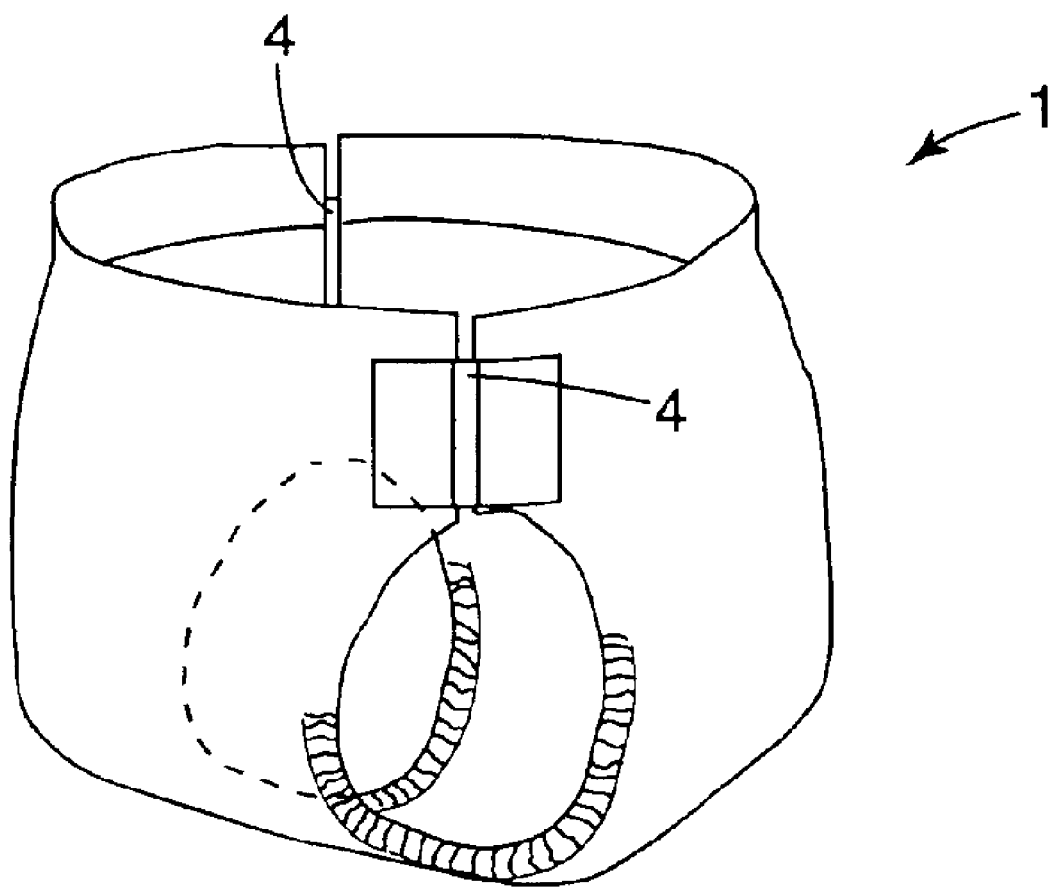
FIG. 1 is a perspective view of a disposable absorbent article using the invention elastic tab closure.

FIG. 1 shows the invention elastic closure tab 4 in use on a disposable absorbent article 1. The elastic closure tab is extended and attached at two opposing side regions of the disposable absorbent article 1.

As shown in FIGS. 2–3, the nonwoven elastic laminate closure tab 4 of the invention comprises adjacent first 20 and second 21 nonwoven closure elements each having a first face (31, 33) and a second face (32, 34) and a coextruded film elastic 10 attached to each closure element first face (31, 33). The first face (31, 32) of each closure element has a first area (23, 25) coated with a pressure sensitive adhesive (14, 19) and a second area (24, 26) adjacent the first area (23, 25) free of pressure-sensitive adhesive at terminal ends (36, 37) of the nonwoven closure elements (20, 21). The coextruded film elastic 10 has two first regions (11, 12) each having at least one inelastic zone and a second region 13 between the two first regions having at least one elastic zone. The two opposing first regions (11 and 12) are attached to the two pressure-sensitive adhesive coated areas (23, 25) of the two closure elements (20, 21) respectively such that the second adhesive free areas (24, 26) of the two adjacent closure elements (20, 21) are in face to face contact with at least a portion of the coextruded elastic film 10 elastic second region 13. The pressure-sensitive adhesive layer (14, 19) is provided with a first region (16, 17), attached to the coextruded elastic film 10 first region (11, 12), and a second adhesive region (15, 18) free for attachment to other elements. The layers are all of a thickness such that the thickness variation across the closure tab 4 is preferably less than about 50 percent, and most preferably less than about 40%.

Figure 4:
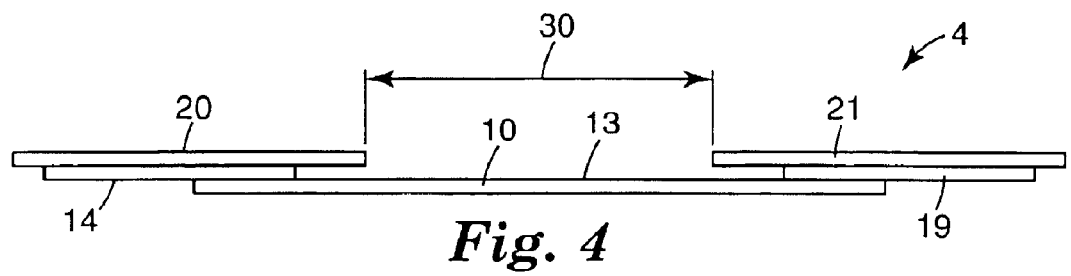
FIG. 4 is a side view of the invention tab closure in an extended condition.
Figure 5:
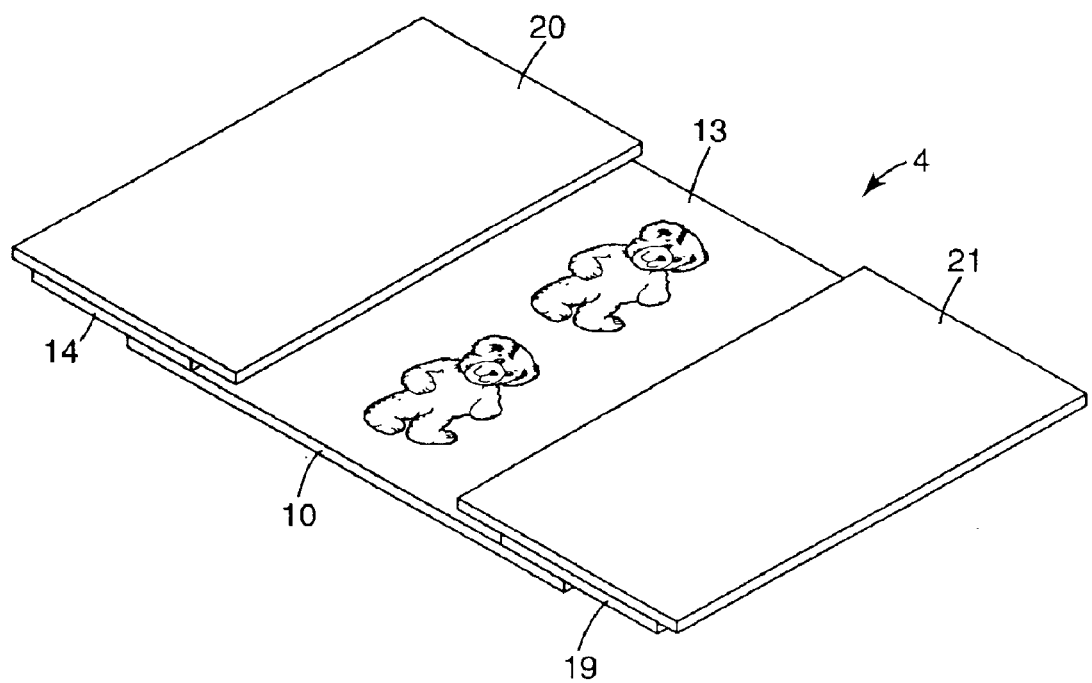
FIG. 5 is a perspective of the invention tab closure in an extended condition.

The two adjacent closure element second adhesive free zones (24, 26) form the opposing terminal ends (36, 37) of the closure elements (20, 21) and are preferably in an abutting face to face relation such that they cover substantially all the elastic film second region 13 as shown in FIGS. 2 and 3. In this way, the elastic film second region 13 is covered prior to use to protect it from adhesive contamination while also minimizing thickness variation across the closure tab 4 in the central region of the closure tab. There are also functional and aesthetic advantages. The elastic can be colored differently than the closure elements or provided with designs so as to provide distinct visual contrast. When the user extends the tab as shown in FIGS. 4 and 5, by a distance 30, the previous covered elastic 13 is then clearly exposed. This provides a clear visual indication of the extent to which the elastic is stretched which is also a direct indication of the force being applied by the elastic. When two opposing tabs are used, the level of force could then be easily adjusted so that each tab is extended to the same degree. Generally, one can easily see when the elastic is being used and adjust the degree of stretch as appropriate.

The closure element terminal ends (36, 37) can either be separably attached or not attached as appropriate. If separably attached, such as by a serrated cut line, they should be easily separated with a minimum level of force. In any event, generally, the adjacent closure elements terminal ends (36, 37) should be less than 5 mm apart, preferably less than 3 mm apart and most preferably in a directly abutting relation.

A unique advantage of the invention construction is that the closure elements and elastic members are relatively thin and coextensive, however the elastic is generally substantially thinner than the closure element. Generally, the closure elements (20, 21) have a thickness of from 0.05 mm to 1.0 mm; preferably 0.1 mm to 0.5 mm. Generally, the film elastic 10 has a thickness of 0.03 mm to 0.5 mm; preferably 0.05 mm to 0.2 mm. Further, the film elastic 10 generally has a thickness of 20 to 60 percent of the thickness of the closure elements, preferably 20 to 50 percent.

The closure elements (20, 21) are preferably a laminate of a nonwoven and a film layer. The nonwoven provides softness while the film layer provides a barrier for the adhesive and/or dimensional stability. The nonwoven preferably is a spunbond nonwoven, having a basis weight from 20 gsm to 50 gsm, where the film layer is extrusion laminated to the spunbond nonwoven. The film layer can have a thickness of from 0.03 mm to 0.5 mm and is preferably adjacent the pressure-sensitive adhesive layer. The film layer can also be separately provided and adhesive laminated, sonic bonded or otherwise conventionally attached to the nonwoven layer. The pressure-sensitive adhesive layers are provided on the closure elements to both attach the film elastic to the closure elements (the first adhesive region 16, 17) and further to attach the closure elements to the disposable garment, or other article, on which it may be used or to other elements (the second adhesive regions 15, 18). Preferably one and most preferably both closure elements have an area beyond the elastic film that has exposed second pressure-sensitive adhesive regions (15, 18) that can be used to attach the closure element or alternatively could be used to attach other elements such as mechanical fastener elements. The second exposed pressure-sensitive adhesive region (15, 18) generally is at least 200 $mm^2$, preferably at least 300 $mm^2$. The first pressure-sensitive adhesive region is generally at least 5 mm wide, preferably at least 10 mm wide.

The elastic film first regions (11, 12) generally have at least one zone that is inelastic to provide for secure adhesion to the closure elements (20, 21). This inelastic zone extends generally at least 0.5 mm, preferably at least 1 mm to 10 mm or more and would in a preferred embodiment would extend over the entire area attached to the first adhesive region. This provides for secure adhesion of the elastic film to the first adhesive regions (16, 17) without excessive use of the elastic material. The second elastic region 13 of the coextruded film elastic generally is from 10 to 30 mm, preferably from 15 to 25 mm for most uses in a disposable absorbent article. The second elastic region would have at least one or more elastic zones. The size of the elastic region selected of course depends on the size of the article being used with the tab and the exact nature of the article, its intended adjustability and the elastic forces required. The elastic region could be formed of at least one elastic zone, which could extend at least 0.5 mm, preferably at least 1 to 10 mm or more. The elastic zones, if not continuous, would be separated by inelastic zones. The use of inelastic zones in the elastic region would be useful in adjusting the elastic properties of the elastic region.

The overall length 40 of the closure element 13 also can vary greatly depending on the desired end use. Generally, the closure elements will be 40 to 100 mm, preferably 50 to 80 mm. The width 41 of the closure elements depends on the desired use and the width can be made to vary as is known in the art for differing functional attributes.

The coextruded elastic film 10 is preferably an elastomeric laminate comprising at least one elastomeric core layer and at least one relatively nonelastomeric outer layer. When selected regions of the skin layer are stretched beyond its elastic limit and relaxed, the surface of the film becomes microstructured and the elastomeric core in this area is formed into an elastic region.

The elastomer forming the elastomeric layer can broadly include any material which is capable of being formed into a thin film layer and exhibits elastomeric properties at ambient conditions. Elastomeric means that the material will substantially resume its original shape after being stretched. Further, preferably, the elastomer will sustain only small permanent set following deformation and relaxation which set is preferably less than 20 percent and more preferably less than 10 percent of the original length at moderate elongation. Generally, any elastomer is acceptable which is capable of being stretched to a degree that causes relatively consistent permanent deformation in a relatively inelastic skin layer. This can be as low as 50% elongation. Preferably, however, the elastomer is capable of undergoing up to 300 to 1200% elongation at room temperature, and most preferably up to 600 to 800% elongation at room temperature. The elastomer can be both pure elastomers and blends with an elastomeric phase or content that will still exhibit substantial elastomeric properties at room temperature.

Preferred elastomers include block copolymers which are elastomeric such as those known to those skilled in the art as A-B or A-B-A block copolymers. These block copolymers are described, for example, in U.S. Pat. Nos. 3,265,765; 3,562,356; 3,700,633; 4,116,917 and 4,156,673, the substance of which are incorporated herein by reference. Styrene/isoprene, butadiene or ethylene-butylene/styrene (SIS, SBS or SEBS) block copolymers are particularly useful. Other useful elastomeric compositions can include elastomeric polyurethanes, ethylene copolymers such as ethylene vinyl acetates, ethylene/propylene copolymer elastomers or ethylene/propylene/diene terpolymer elastomers. Blends of these elastomers with each other or with modifying non-elastomers are also contemplated. For example, up to 50 weight percent, but preferably less than 30 weight percent, of polymers can be added as stiffening aids such as polyvinylstyrenes, polystyrenes such as poly(alpha-methyl) styrene, polyesters, epoxies, polyolefins, e.g., polyethylene or certain ethylene vinyl acetates, preferably those of higher molecular weight, or coumarone-indene resin. The ability to use these types of elastomers and blends provides the invention laminate with significant flexibility.

Viscosity reducing polymers and plasticizers can also be blended with the elastomers such as low molecular weight polyethylene and polypropylene polymers and copolymers, or tackifying resins such as Wingtack™, aliphatic hydrocarbon tackifiers available from Goodyear Chemical Company. Tackifiers can also be used to increase the adhesiveness of an elastomeric layer to a skin layer. Examples of tackifiers include aliphatic or aromatic hydrocarbon liquid tackifiers, polyterpene resin tackifiers, and hydrogenated tackifying resins. Aliphatic hydrocarbon resins are preferred.

The relatively inelastic skin layer is preferably formed of any semi-crystalline or amorphous polymer that is less elastic than the core layer(s) and will undergo permanent deformation at the stretch percentage that the elastomeric laminate will undergo. Therefore, slightly elastic compounds, such as some olefinic elastomers, e.g. ethylene-propylene elastomers or ethylene-propylene-diene terpolymer elastomers or ethylenic copolymers, e.g., ethylene vinyl acetate, can be used as skin layers, either alone or in blends. However, the skin layer is generally a polyolefin such as polyethylene, polypropylene, polybutylene or a polyethylene-polypropylene copolymer, but may also be wholly or partly polyamide such as nylon, polyester such as polyethylene terephthalate, polyvinylidene fluoride, polyacrylate such as poly(methyl methacrylate) and the like, and blends thereof. The skin layer material can be influenced by the type of elastomer selected. If the elastomeric layer is in direct contact with the skin layer the skin layer should have sufficient adhesion to the elastomeric core layer such that it will not readily delaminate.

Additives useful in the skin layer include, but are not limited to, mineral oil extenders, antistatic agents, pigments, dyes, antiblocking agents, provided in amounts less than about 15%, starch and metal salts for degradability and stabilizers such as those described for the elastomeric core layer.

Other layers may be added between the core layer and the outer layers, such as tie layers to improve the bonding of the layers. Tie layers can be formed of, or compounded with maleic anhydride modified elastomers, ethyl vinyl acetates and olefins, polyacrylic imides, butyl acrylates, peroxides such as peroxypolymers, e.g., peroxyolefins, silanes, e.g., epoxysilanes, reactive polystyrenes, chlorinated polyethylene, acrylic acid modified polyolefins and ethyl vinyl acetates with acetate and anhydride functional groups and the like, which can also be used in blends or as compatiblizers in one or more of the skin or core layers. Tie layers are particularly useful when the bonding force between the skin and core is low. This is often the case with polyethylene skin as its low surface tension resists adhesion. However, any added layers must not significantly affect the microstructuring of the skin layers.

To provide for adjacent elastic and inelastic zones it is possible to either vary the skin layer or elastic layer in these regions or zones so that only certain areas are capable of being or becoming elastic. In an extreme case, the elastic core layer an be absent from a region or substantially thicker in a region to cause that region or zone to form an inelastic area such as described in U.S. Pat. No. 5,057,097 (Gesp) or U.S. Pat. No. 5,773,374 (Wood et al.), the substance of which are incorporated herein by reference in their entirety. Alternatively, the elastic or skin layers can be treated in zones to weaken or strengthen them to provide elastic or inelastic zones, respectively. For example, zones or regions can be controlled to have lower overall modulus values that will preferentially yield before adjacent, in the direction of an orienting stress, higher modulus regions. This modulus control can be accomplished by a variety of methods that can involve the prelaminate formation stages, the formation stage, or post formation treatment of a particular laminate or laminate intermediate. Similarly, localization of stress, applied to the whole laminate, can result in preferential elongation in areas containing these localized stress regions. This stress control can also be effected by a variety of methods in any of a multitude of stages in the formation of the laminate. These strengthening or weakening treatments can include post formation annealing, selective crosslinking or selective plasticization, localized corona treatment, mechanical ablation, scoring, cutting out laminate material or indentation or the like, specific elastic zones can also be formed by controlled localized stretching as disclosed in U.S. Pat. No. 5,344,691 (Hanschen), the substance of which is incorporated by reference in its entirety.

After forming a zone activatable elastic laminate, the laminate is stretched past the elastic limit of the skin layer(s) exclusively or preferably in the lower modulus or preferred stress regions, which deform. The zone activated laminate then is recovered instantaneously, with time or by the application of heat. For heat activated recovery the inherent temperature of heat activation is determined by the materials used to form the elastic layer of the laminate in the first instance. However, for any particular laminate the activation temperature can be adjusted by varying the skin/core ratio of the laminate, adjusting the percent stretch or the overall laminate thickness. The activation temperature used for a heat shrink laminate is generally at least 80° F. (26.7° C.).

Activation will generally be accomplished by stretching the laminate in a direction substantially transverse to a primary extent of the film having spaced zones or regions of differing modulus or stress characteristics. At least one inelastic zone will be in the first region (11, 12) of the film attached to the closure element. At least one elastic zone will be in the second region 13 unattached to the closure elements. Preferably inelastic zones will form at least 10 percent of first regions (11, 12), preferably at least 50 percent and in a preferred embodiment 100 percent. Preferably elastic zones will form at least 50 percent of the second region 13, preferably at least 80 percent and in a preferred embodiment 100 percent.

Test Methods

Shear Adhesion

A shear adhesion test was used to demonstrate the improvement in bond strength resulting from the adhesive bonding of a closure element nonwoven tape to an annealed elastic film. The shear adhesion was measured by determining the length of time it took for a 40 mm×40 mm sample of nonwoven tape to shear off of an elastic film test substrate under a 0.5 kilogram load. A 40 mm×65 mm piece of the elastic film substrate (cut such that the 65 mm dimension was in the cross-direction of the web) was laminated on both sides to a 90 mm×50 mm piece of reinforcing tape (KN-1759, available from 3M Company) by folding over the reinforcing tape to sandwich the elastic film in order to enhance the stiffness of the substrate. A 25 mm section of the 65 mm length was left unreinforced. A 40 mm×40 mm piece of nonwoven fastening tape (described below) was laminated to the unreinforced end of the elastic film by rolling it down onto the elastic film using four passes of a 5 kg hard rubber roller. The overlap region between the nonwoven tape and the elastic film was 12 mm×40 mm. The nonlaminated end of the nonwoven tape was reinforced with a 90 mm×50 mm piece of reinforcing tape (KN-1759, available from 3M Company) by folding over and stapling the reinforcing tape to sandwich the nonwoven tape. A small loop was left in the fold region of the reinforcing tape such that a brass hook could be slid into it. A 0.5 kilogram weight was hung from one end of the brass hook, generating a shear load in the overlap region at a 180° angle. The laminated elastic film and nonwoven tape were hung vertically in a 38° C. oven. The time that it took in minutes for the bond in the overlap region to fail and the weight to drop was recorded in Table 1 below as a measure of the shear adhesion. Reported values are averages of 4 tests.

Laminates of the elastic film to the nonwoven tape were also prepared as above but were additionally heat bonded in the overlap region using a Sentinel Brand Heat Press Model 808 set at 93° C. for approximately 1 second at a pressure of 4.9 kg/cm$^2$ ("Heated Lamination") followed by shear testing.

Nonwoven Tape

The nonwoven tape was produced with a backing consisting of a 50 gram/m$^2$ polypropylene spunbond nonwoven web extrusion laminated to a 28 gram/m$^2$ polypropylene/polyethylene blended film. A 38 gram/m$^2$ pressure sensitive adhesive consisting of 50% Kraton 1119 (Kraton Polymers, Inc.) and 50% Wingtack Plus (Goodyear Chemical) was hot melt coated onto the film side of the backing. A solvent based silicone polyurea was used as a release coating on the nonwoven side of the backing.

EXAMPLES & COMPARATIVES

Comparative C1

A three layer coextruded elastic film was prepared as described in U.S. Pat. No. 5,468,428 Example 1 except the two outer layers were made with 5E57 polypropylene (Dow Chemical) and the core elastomeric layer was made with a blend of 70% Kraton 1114 SIS block copolymer (Kraton Polymers) and 30% 678C polystyrene (Dow Chemical). The thickness of each of the outer layers was 9 microns and the thickness of the core layer was 53 microns. The film was stretched in the cross-direction of approximately 6:1 to overstretch the outer layers and allowed to recover, thus rendering the entire film elastic. The film was elastic throughout its entire width and contained no inelastic annealed zones.

Example 1

An elastic film was prepared as in C1 above and subsequently stretched 6:1 in the cross-direction and then annealed with parallel longitudinal bands by passing the film over a patterned heated roll set at approximately 80° C. The inelastic annealed zones consisted of machine direction stripes 1.5 mm wide and 1 mm apart. The overlap region for the shear test described above contained approximately 50% annealed elastic film (inelastic zones) laminated to the nonwoven tape.

Example 2

An elastic film was prepared as in C1 above and subsequently stretched 6:1 in the cross-direction and then allowed to relax. The film was then stretched 4:1 and clamped into a fixture. A 5 cm wide inelastic zone was annealed in the middle of the clamped sample using a Sentinel Brand Heat Press equipped with a 5 cm wide sealing bar set at 121° C. using a pressure of 4.9 kg/cm$^2$ for approximately 1 second. The overlap region for the shear test described above contained 100% annealed elastic film (inelastic zones) laminated to the nonwoven tape.

TABLE 1

| Material | % Annealed Bond Area | Heated Lamination (Y/N) | Shear Failure Time (minutes) |
|---|---|---|---|
| C1 | 0 | N | 4 |
| C1 | 0 | Y | 21 |
| 1 | 50 | N | 143 |
| 1 | 50 | Y | 380 |
| 2 | 100 | N | >7100* |
| 2 | 100 | Y | >7100* |

*test was discontinued at 7100 minutes

Table 1 shows that the bond strength between an elastic film and an adhesive tape is dramatically improved when the elastic film is annealed in the bonding region.

What is claimed is:

1. A elastic laminate closure tab comprising adjacent first and second nonwoven closure elements each having a first face and a second face and a elastic film attached to each closure element first face, wherein the first face of each nonwoven closure element has a first area coated with a pressure sensitive adhesive and a second area adjacent the first area free of pressure-sensitive adhesive which second area includes terminal ends of the nonwoven closure elements, the elastic film has two opposing first regions each having inelastic zones and a second region between the two first regions having elastic zones, wherein the elastic film two opposing first regions are adhesively attached to the two pressure-sensitive adhesive areas on the first face of the two nonwoven closure elements respectively such that the second adhesive free areas on the first face of the two adjacent nonwoven closure elements are in face to face contact with at least a portion of the elastic film elastic second region and wherein the thickness variation across the closure tab is less than 50 percent.

2. The elastic laminate closure tab of claim 1 wherein the two adjacent nonwoven closure elements second adhesive free areas form the opposing terminal ends of the closure elements and are in a substantially abutting face to face relation such that the nonwoven closure element second areas cover substantially all the elastic film elastic second region and the elastic film is a coextruded elastic film having an elastic layer and at least a second layer.

3. The elastic laminate closure tab of claim 2 wherein the abutting nonwoven closure element terminal elements are separably attached.

4. The elastic laminate closure tab of claim 2 wherein the nonwoven abutting closure element terminal elements are not attached.

5. The elastic laminate closure tab of claim 2 wherein the thickness variation across the closure tab is less than 40 percent.

6. The elastic laminate closure tab of claim 1 wherein the nonwoven closure elements have a thickness of from 0.05 mm to 1.0 mm.

7. The elastic laminate closure tab of claim 6 wherein the elastic film has a thickness of 0.03 mm to 0.5 mm.

8. The elastic laminate closure tab of claim 7 wherein the elastic film has a thickness of 20 to 60 percent that of the closure elements.

9. The elastic laminate closure tab of claim 1 wherein the nonwoven closure elements are laminates of a nonwoven and a film layer.

10. The elastic laminate closure tab of claim 9 wherein the film layer is extrusion laminated to the spunbond nonwoven.

11. The elastic laminate closure tab of claim 2 wherein the pressure-sensitive adhesive can be exposed on at least one closure element for attachment to a further substrate.

12. The elastic laminate closure tab of claim 11 wherein the pressure-sensitive adhesive is exposed on both nonwoven closure elements.

13. The elastic laminate closure tab of claim 11 wherein the exposed pressure-sensitive adhesive is at least 200 mm2.

14. The elastic laminate closure tab of claim 11 wherein the pressure-sensitive adhesive on at least one closure element is adhesively attached to an attachment element.

15. The elastic laminate closure tab of claim 14 wherein the attachment element is a hook element.

16. The elastic laminate closure tab of claim 2 wherein the inelastic zone(s) in the first region are at least 0.5 mm wide.

17. The elastic laminate closure tab of claim 2 wherein the total inelastic zone(s) in the first region are at least 10 percent of the first region area.

18. The elastic laminate closure tab of claim 2 wherein the total inelastic zone(s) in the first region are at least 50 percent of the first region area.

19. The elastic laminate closure tab of claim 1 wherein the total elastic zones in the second region are at least 50 percent of the second region area.

20. A stable roll of an elastic laminate for forming closure tabs comprising adjacent first and second nonwoven closure elements each having a first face and a second face and a elastic film attached to each nonwoven closure element first face, wherein the first face of each nonwoven closure element has a first area coated with a pressure sensitive adhesive and a second area adjacent the first area free of pressure-sensitive adhesive which second area includes terminal ends of the closure elements, the elastic film has two opposing first regions each having inelastic zones and a second region between the two first regions having elastic zones, wherein the elastic film two opposing first regions are adhesively attached to the two pressure-sensitive adhesive areas on the first face of the two nonwoven closure elements respectively such that the second adhesive free areas on the first face of the two adjacent nonwoven closure elements are in face to face contact with at least a portion of the elastic film elastic second region and wherein the thickness variation across the closure tab is less than 50 percent.

21. The stable roll of an elastic laminate for forming closure tabs of claim 20 wherein the two adjacent nonwoven closure elements second adhesive free areas form the opposing terminal ends of the nonwoven closure element, and are in a substantially abutting face to face relation such that the nonwoven closure element second areas cover substantially all the elastic film elastic second region and the elastic film is a coextruded elastic film having an elastic layer and at least a second layer.

22. The stable roll of an elastic laminate for forming closure tabs of claim 21 wherein the abutting nonwoven closure element terminal elements are separably attached.

23. The stable roll of an elastic laminate for forming closure tabs of claim 21 wherein the abutting nonwoven closure element terminal elements are not attached.

24. The stable roll of an elastic laminate for forming closure tabs of claim 21 wherein the thickness variation across the closure tab is less than 40 percent.

25. The stable roll of an elastic laminate for forming closure tabs of claim 20 wherein the closure elements have a thickness of from 0.05 mm to 1.0mm.

26. The stable roll of an elastic laminate for forming closure tabs of claim 25 wherein the elastic film has a thickness of 0.03 mm to 0.5 mm.

27. The stable roll of an elastic laminate for forming closure tabs of claim 25 wherein the elastic film has a thickness of 20 to 60 percent that of the closure elements.

28. The stable roll of an elastic laminate for forming closure tabs of claim 25 wherein the nonwoven closure elements are laminates of a nonwoven and a film layer.

* * * * *